United States Patent
Abarzúa

(10) Patent No.: US 6,777,183 B2
(45) Date of Patent: Aug. 17, 2004

(54) PROCESS FOR ALLELE DISCRIMINATION UTILIZING PRIMER EXTENSION

(75) Inventor: Patricio Abarzúa, West Caldwell, NJ (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

(21) Appl. No.: 09/827,289

(22) Filed: Apr. 5, 2001

(65) Prior Publication Data

US 2002/0009716 A1 Jan. 24, 2002

Related U.S. Application Data

(60) Provisional application No. 60/194,843, filed on Apr. 5, 2000.

(51) Int. Cl.⁷ .......................... C12Q 1/68; C12P 19/34; C07H 21/02
(52) U.S. Cl. .................. 435/6; 435/91.1; 435/91.2; 536/23.1; 536/24.8; 536/24.31; 536/24.32; 536/24.33
(58) Field of Search .......................... 435/6, 91.1, 91.2; 536/23.1, 24.3, 24.31, 24.33

(56) References Cited

U.S. PATENT DOCUMENTS 5,710,028 A * 1/1998 Eyal et al. .................. 435/91.1
6,355,431 B1 * 3/2002 Chee et al. .................. 435/6

FOREIGN PATENT DOCUMENTS

| WO | WO 90/11372 | 10/1990 |
| WO | WO 97/07235 | 2/1997 |

OTHER PUBLICATIONS

Ishikawa et al, "Sequence based typing of HLA–A2 alleles using a primer with an extra base mismatch", Human Immunology, 42:315–318 (1995).*

Sasvari–Szekely et al., Rapid Genotyping of Factor V Leiden Mutation Using Single–Tube Bidirectional Allele Specific Amplification . . . Electrophoresis, vol. 21, pp. 816–821 (2000).

Lizardi, et al., "Mutation detection and single–molecular counting using isothermal rolling–cirle amplification," Nature Genetics, vol.; 19, pp. 225–232 (Jul. 19, 1998).

Valimaa et al, Detection of HLA–B27 Alleles by Group Specific Amplification and Time–Resolved Fluorimetry, J. Immunological Methods, vol. 219, pp. 131–137 (1998).

* cited by examiner

Primary Examiner—Jeffrey Fredman
(74) Attorney, Agent, or Firm—Elliot M. Olstein; Alan J. Grant

(57) ABSTRACT

Disclosed are methods for allele discrimination involving the use of rolling circle amplification (RCA) coupled with primer extension and utilizing exonuclease deficient polymerases to distinguish matched and unmated single nucleotide sites, such as in the case of a single nucleotide polymorphism (SNP).

20 Claims, 4 Drawing Sheets

Allele Discrimination Factor

|  |  | G542X | M1101K |
|---|---|---|---|
| WT Target | 15-mer | 178 | 50 |
|  | 20-mer | 19 | 42 |
|  | 30-mer | 2.4 | 5.3 |

|  |  | G542X | M1101K |
|---|---|---|---|
| Mutant Target | 15-mer | 21 | weak signal |
|  | 20-mer | 8.1 | 55 |
|  | 30-mer | 1.5 | 30 |

PROCESS FOR ALLELE DISCRIMINATION UTILIZING PRIMER EXTENSION

This application claims priority of U.S. Provisional Application 60/194,843, filed Apr. 5, 2000, the disclosure of which is hereby incorporated by reference in its entirety.

FIELD OF THE INVENTION

The present invention relates to a process for allele discrimination employing primer extension using an exonuclease deficient polymerase to distinguish matched 3'-ends from mismatched 3'-ends of hybridized primer and target oligonucleotides.

BACKGROUND OF THE INVENTION

Many diseases are known which have a genetic basis in their etiology and result from the occurrence of mutations in gene sequences present in the genomes of different organisms, especially animals, including humans, afflicted with such diseases. Consequently, methods for detecting slight genetic differences, as small as one nucleotide (called single nucleotide polymorphisms or SNPs), between the genome of a healthy individual and that of a person afflicted with a genetic defect can prove highly valuable in elucidating the nature and causes of such condition. More importantly, obtaining valuable information about such conditions is greatly enhanced if a sensitive process is available for determining small genetic defects, such as a difference of one nucleotide at a particular location in the genome.

A genome is composed of different loci which are themselves composed of one or more genes, which genes may contain variations, so-called alleles, for each system. For example, the immunoglobulin superfamily, which includes, inter alia, the T-cell receptor, the immunoglobulin and the HLA (or human leukocyte antigen) systems, is characterized by the presence of large sequence variations (called polymorphisms). Defects in the immune response, which are due to diverse variations in one or more of the gene arrangements of such systems, may result in disease. Conversely, diseases like cystic fibrosis show varying and complex genetic variations in DNA sequence. Genetic variation may therefore be linked to diseases and their symptoms. Identification of the associated alleles, especially differences in those alleles, may be important in determining the risk of a disease associated with genetic markers or in detecting variations in genes that result in some other malady. Further, the delineation of slight genetic differences can be readily utilized for the diagnosis (even treatment) of certain diseases, as well as furthering efforts toward prevention by identifying persons having the greatest risk of a particular disease. The latter is a critical factor in those situations where early treatment is possible and the development of the disease can be retarded.

Several methods for detecting specific nucleotide variations and genetic polymorphisms in nucleic acids are known. For example, some methods comprise amplifying nucleic acid sequences having nucleotide variations, mutations and polymorphisms, with subsequent detection thereof using allele specific oligonucleotide sequences and a dot blot. This process utilizes allele-specific oligonucleotide sequences that have to be very specific for the nucleotide variation to be detected and offers numerous primer sequences for use therein depending on the DNA sequence to be studied. [See, for example, EP-A-237,362]

R. K. Saiki et al., *Proc. Natl. Acad. Sci. USA*. 86, 6230–6234 (1989) as well as WO 89/11548 both disclose use of immobilized sequence-specific oligonucleotides. WO 89/11547 discloses methods for determining genotypes having different alleles in the HLA-DP loci. This latter method operates by hybridizing nucleic acid samples with a series of probes which are specific for various segments.

U.S. Pat. No. 5,912,148 discloses a polymerase chain reaction (PCR) method as well as an oligonucleotide ligase assay (OLA) procedure for analyzing complex genetic systems in a single reaction vessel (also see other methods cited therein). This method seeks to determine the products of the OLA reaction using various OLA and PCR probes.

U.S. Pat. No. 5,759,771 discloses a method for determining genotypes by comparing the nucleotide sequences of members of a gene system that flank the polymorphic segments of a particular genetic locus. Here, the compared sequences contain conserved sequences used to amplify the strongly conserved segments from different sources. These are then compared as a means of establishing genotype.

U.S. Pat. No. 5,710,028 discloses a method of simultaneous determination of the identity of nucleotide bases at specific locations in nucleic acids of interest but relies on the use of extension blocking agents, commonly dideoxynucleoside triphosphates, to prevent extension in cases where there is a particular nucleotide present at a given location within the target sequence (the latter acting as a template). A similar process is used in U.S. Pat. No. 6,013,431.

Nucleic acid sequence analysis has become important in many research, medical, and industrial fields and a host of methods have been described in the literature. Heretofore, many of these approaches have been motivated by the development of various methods for amplifying target nucleic acids, e.g. polymerase chain reaction (PCR) of U.S. Pat. No. 5,137,806, ligation chain reaction (LCR), and the like, as well as rolling circle amplification (RCA) (See, for example, U.S. Pat. No. 5,854,033; Lizardi et al, *Nature Genetics*, 19, 225–232 (1998). Such amplification techniques are certainly useful as the basis for developing sensitive and specific diagnostic assays but in some cases these methods may be fairly complex and involved, especially when the system to be analyzed is a complex one, such as a complex genetic system, for example, the highly variable cystic fibrosis locus. Because it may be difficult to identify the amplified product in such systems, post-amplification manipulations may often be necessary, especially in cases other than RCA. One approach used to avoid these problems is that of the oligonucleotide ligation assay (OLA). [U.S. Pat. No. 4,883,750] Here, oligonucleotides are prepared that are complementary to adjacent regions of a target sequence and are capable of hybridizing to the target so that they lie end-to-end and can be ligated when no mismatches occur at or near the contiguous ends. Whenever mismatches occur, ligation is precluded. The result is a set of oligonucleotide pairs that are perfect complements of all the allelic variants of interest at a given locus. By carefully selecting the labeling method, a wide range of alleles can be specifically identified in a single assay. However, such assays can be complicated. [Nickerson et al., *Proc. Natl. Acad. Sci. USA* 87:8923–8927 (1990)]

Other methods for allele discrimination have relied on template dependent ligation of two adjacent short oligonucleotides. One such oligonucleotide consists of a reverse polarity oligonucleotide containing a primer for RCA and a short target specific sequence terminating at an allele-specific 3'-end residue. A second oligonucleotide is immobilized on a glass slide and anneals next to the target specific oligonucleotide sequence. Template dependent and allele-specific ligation anchors the RCA platform to the slides. Following RCA, products are detected by standard fluorescent and immunochemical techniques. The use of allele specific primers annealing to different circles allows simultaneous detection of various alleles (called multiplexing). Such methods rely on a ligation step as the allele discrimination event. (see Lizardi et al, supra)

A different method employs RCA using padlock probes to detect mutations in cytological samples. However, padlock probes are not always advantageous due to steric hindrance and topological constraints on DNA targets. Such procedures also rely on a ligation step. [see: Nilsson et al, Padlock Probes: Circularizing Oligonucleotides for Localized DNA Detection, *Science*, 265, 2085–2088 (1994)]

One approach to simplifying these procedures is to eliminate some of the steps, thereby simplifying and speeding the overall procedure. For example, such procedures have the disadvantage of relying on DNA ligation as the allele discrimination step.

The method according to the present invention overcomes these problems while having the overall advantage of being highly efficient and sensitive to single copy genes as well as being sensitive to single mutations (i.e., SNPs). More specifically, advantages include the fact that new mutations can be detected directly and can then be investigated in more detail for functionality (as opposed to mere serological testing of mutated polypeptides and polynucleotides). In addition, the method is simple and thus can be made widely available for use, it can readily be automated for large scale assays, or provided as a kit for manual and spot determinations, or for use in the field, it can be performed either in suspension or using solid supports for ready isolation of products, it is readily amenable to many different methods of detection and is readily adapted to multiplexing so that different alleles, or sets of alleles, can be readily and simultaneously detected. In addition, the methods of the present invention are useful in allele discrimination, detection of SNPs, genotyping, molecular haplotyping and mutation detection, to name but a few of the uses.

BRIEF SUMMARY OF THE INVENTION

The present invention relates to methods of detecting pne or more nucleotides at specific locations within a gene sequence using primer extension by exonuclease deficient polymerase action.

It is therefore one object of the present invention to provide a simple and ready means of genotyping using the ability of a probe to detect mismatches in a target polynucleotide sequence such that the absence of a given mismatch, i.e., a mutated residue, will lead to amplification of a predetermined gene sequence that can be readily detected and wherein the absence of such sequence amplification is a reliable indicator of the presence of a single nucleotide mismatch.

It is a further object of the present invention to provide methods of detecting mismatches at specified nucleotide positions as a means of simple, specific and straightforward allele discrimination as well as for general use in detecting single nucleotide polymorphisms (SNPs), as well as other mutations, and for use in molecular haplotyping.

It is another object of the present invention to provide methods for the amplification of specific gene sequences as a means of detecting mutations in target polynucleotides wherein said target polynucleotides are derived from genomes of animals, especially humans, but also non-humans.

It is still another object of the present invention to provide a means of allele discrimination through rolling circle amplification and tandem DNA sequence formation that is readily amenable to all forms of detection, including by specific probes and labeling agents, especially using fluorescent labels.

It is yet another object of the present invention to provide methods for genotyping through sequence amplification that are readily adaptable to use in suspension, solution or through the use of solid supports for ready isolation of the products of said amplification.

It is yet a still further object of the present invention to provide methods useful in multiple allele discrimination through procedures readily susceptible to known multiplexing techniques, thereby facilitating the simultaneous detection of different alleles in a sample and limited only by the number of fluorophore detectors available and the equipment available for detection.

In another embodiment, the present invention is directed to kits for carrying out the methods of the invention. Preferably, such kits include (a) a plurality of oligonucleotide probes, each oligonucleotide probe of said plurality being capable of hybridizing to one or more target polynucleotides that may or may not possess a mismatch with respect to a terminal residue of the oligonucleotide probes; (b) a sample of an exonuclease deficient DNA polymerase; (c) a plurality of amplification primers, each said primer being capable of hybridizing to an elongated segment of said oligonucleotide probe as well as comprising a primer sequence complementary to a sequence on an amplification target circle (ATC) for use in rolling circle amplification; (d) a sample of amplification target circles (ATC), essentially single stranded DNA circles, comprising a sequence of 10 to 20, even 30, nucleotides in length, which sequence is complementary to a sequence of the amplification primers of part (c) and which ATCs act as templates for rolling circle amplification (RCA); (e) a sample of a DNA polymerase capable of carrying out rounds of rolling circle amplification, such as T7 DNA polymerase; and (f) a means for detecting the products of rolling circle amplification, including, but not limited to, various labeling reagents and address probes and tags.

Figure 3:
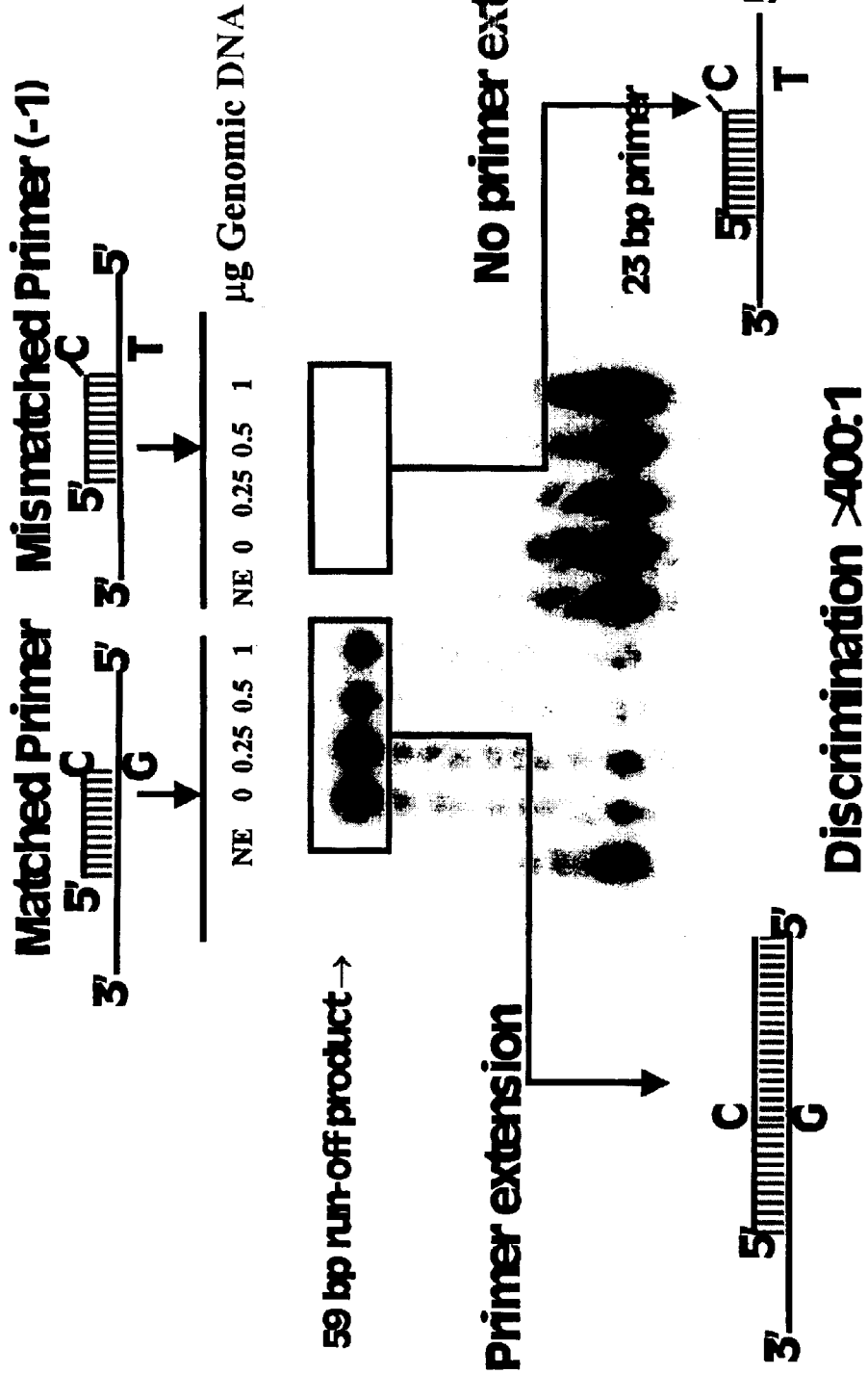

FIG. 3 shows a primer extension experiment using T7 Sequenase in the presence of genomic DNA and using a matched primer and a mismatched primer.

Figure 4:
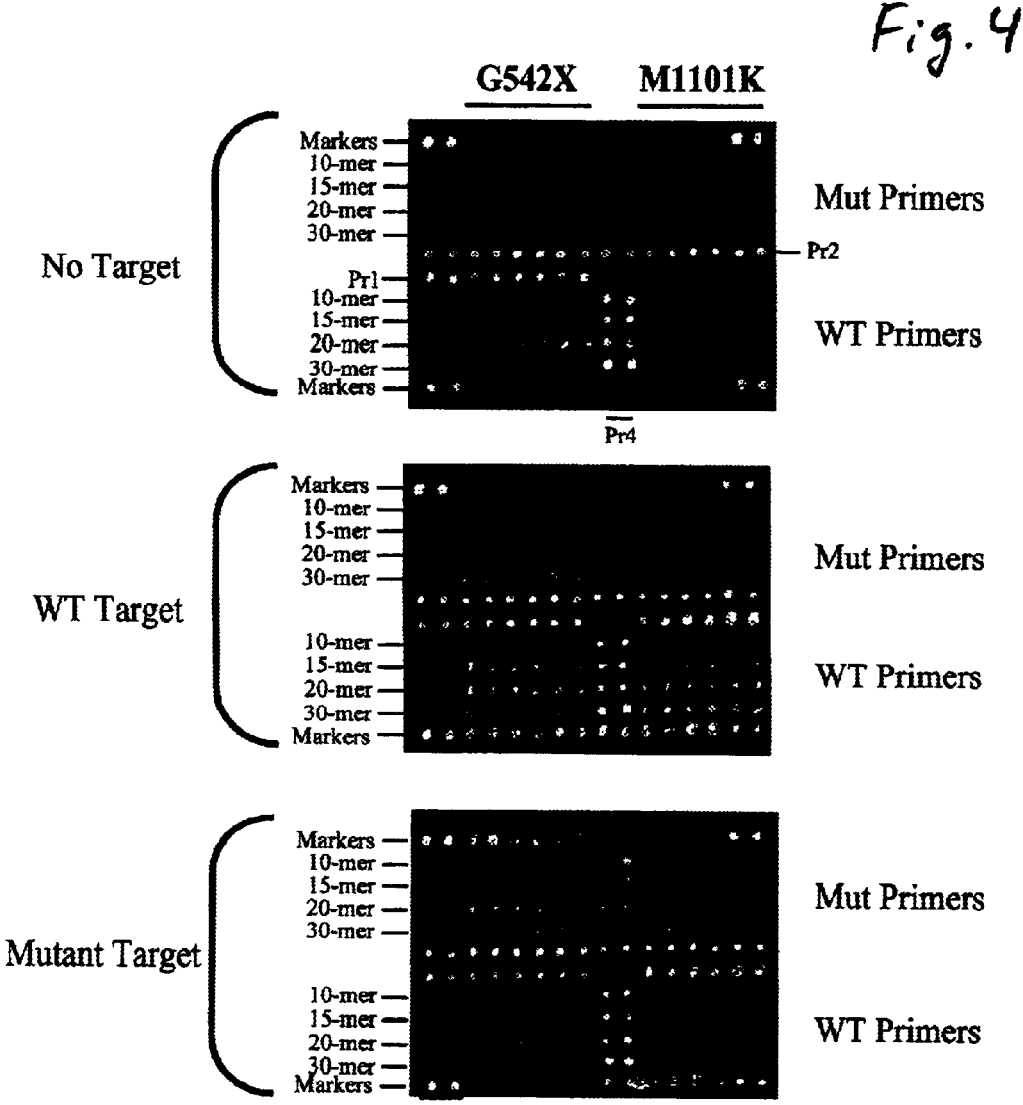

FIG. 4 shows scanned images of microarrays. Pr1, Pr2, and Pr4 are controls for RCA reaction. Markers are Cy3-labelled oligonucleotide spotted on the array for orientation. WT=wild type, Mut=Mutant

DETAILED DESCRIPTION OF THE INVENTION

In general, the present invention relates to methods for simple, quantitative, consistent and more reliable amplification and detection of a target nucleic acid sequence containing an allele different from that of a reference sequence. Using the methods of the present invention, target sequences are amplified via a small primer probe that matches or mismatches a target sequence and then extending the primer probe, removing the target and matching the primer probe with a second probe containing an arbitrary primer binding sequence. This allows consistency in the priming and replication reactions, even between probes having very different target sequences. Additionally, amplification takes place not in cycles, but in a continuous, isothermal rolling circle replication, thereby providing a more reliable, simpler and more consistent output for subsequent detection and identification. The methods of the invention facilitate the detection of mismatched sequences indicative of different alleles, or mutations, in selected target sequences.

In accordance with the disclosure herein, the present invention relates to a process for detecting a single nucleotide polymorphism (SNP) comprising:

(a) contacting one or more allele specific oligonucleotide primers (P1) with one or more target polynucleotides (TP), wherein said target polynucleotide possesses a first portion that is complementary to a second portion located on said P1 at or near one end thereof but wherein the terminal nucleotide, and third nucleotide from the terminal nucleotide, at said end of said P1 may not be complementary to the corresponding nucleotide of said target polynucleotide, and wherein such contacting occurs under conditions that promote hybridization between the first and second portions thereby forming an P1-TP complex;

(b) contacting the P1-TP complex of (a) with an exonuclease deficient deoxyribonucleotide (DNA) polymerase enzyme under conditions that promote extension of the P1 with the TP as template thereby forming an extended segment (ES) of P1; and (c) detecting the extended P1.

The present invention also relates to a process for amplifying and/or detecting extended P1 that includes the previous steps but wherein said process further comprises the additional steps:

(d) removing the target polynucleotide (TP) from said complex;

(e) contacting a primer oligonucleotide (P2) with the extended P1, wherein the primer oligonucleotide comprises a first segment complementary to at least a portion of the extended segment (ES) formed in step (b) and a second segment that includes the 3'-terminus of said primer oligonucleotide (P2) under conditions promoting hybridization of P2 and the extended P1 (EP1) to form an EP1-P2 complex;

(f) contacting an amplification target circle (ATC) with the EP1-P2 complex under conditions that promote hybridization between the amplification target circle and the P2 portion of said EP1-P2 complex to form an EP1-P2-ATC complex; and (g) contacting DNA polymerase with the EP1-P2-ATC complex under conditions that promote replication of the amplification target circle, wherein said replication of the ATC results in the formation of tandem sequence DNA (TS-DNA) thereby indicating the presence of extended P1 (and, in one embodiment of the present invention, wild type target or P1 polynucleotide).

Figure 1:
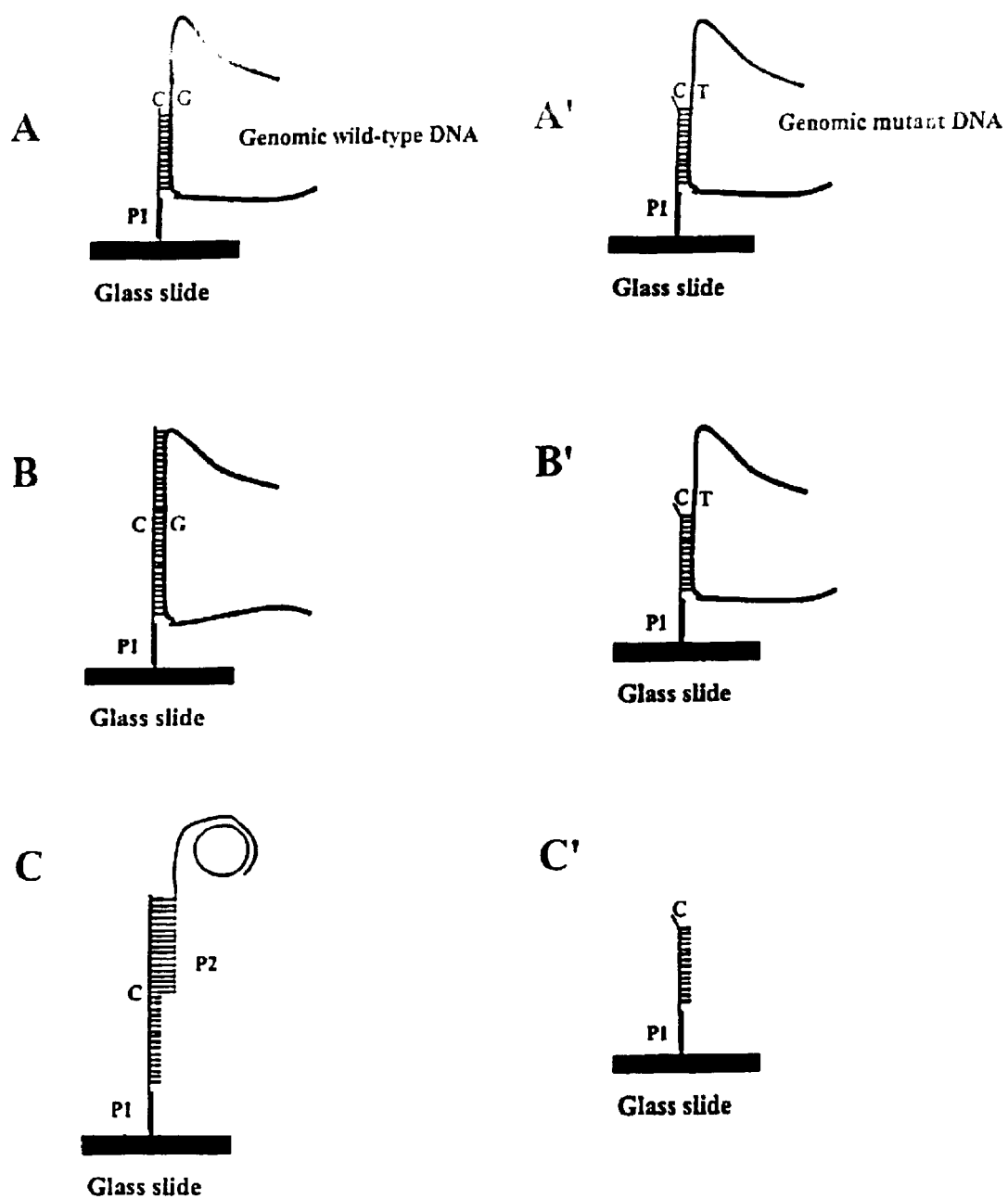
FIG. 1 shows one embodiment of the invention in which genomic wild-type and target DNAs are distinguished by their relative abilities to support extension of primer (designated herein as P1). Wild-type or mutant target DNA is first annealed to an allele-specific P1 primer and the 3'-end of said primer is then extended by an exonuclease-deficient DNA polymerase capable of distinguishing between a matched and mismatched residue at the 3'-end of the P1 oligonucleotide and extending only from a matched nucleotide and using the target DNA as template for said extension (Panel A—wild-type DNA and panel A' —mutant target DNA). Probe P1 is extended by a polymerase enzyme in B (here the wild type allele) but not in B' (here the mutant allele). After target DNA is removed, a short allele-specific bipolar, or bifunctional, primer (designated herein as P2) is annealed (Panel C) to newly synthesized DNA of the extension, which P2 primer serves to anchor the rolling circle amplification (RCA) platform to the slide in an allele-specific manner. In this embodiment, P1 is immobilized on a slide of glass but other substrates are usable within the claimed invention.

FIG. 1 shows an embodiment of the present invention wherein anchorage of a rolling circle amplification (RCA) platform to an immobilized oligonucleotide (P1) is accomplished in a target and allele specific manner. As shown therein, the P1 oligonucleotide (the allele-specific oligonucleotide, or ASO or P1 probe) contains a short target-specific sequence terminating at an allele-specific 3'-end. The target DNA (either genomic wild-type DNA shown in the panels on the left or genomic mutant DNA shown in the panels on the right) anneals to this oligonucleotide (P1) at a point at or near the 3'-end of P1. In accordance with the method of the invention, the 3'-terminal nucleotide of P1 may or may not match the corresponding nucleotide of the target DNA. Thus, in one embodiment of the present invention, in the case of genomic wild-type DNA, as shown in panel A of FIG. 1, there is such a match. In this case, the 3'-terminal nucleotide residue of P1 is a cytosine (C) residue that normally pairs, within the standard Watson-Crick pairing scheme, with a guanine (G) residue (as shown for the target DNA). Conversely, in the case of the mutant DNA (panel A' of FIG. 1) the corresponding target nucleotide is a thymine (T) residue, for which there is no match. Consequently, the terminal 3'-residue of the ASO (P1) is not paired with a complementary nucleotide of the target genomic mutant DNA, thereby giving rise to a mismatch. Following such annealing, the 3'-end of said oligonucleotide (P1) in panel B of FIG. 1 is then extended by limited synthesis using an exonuclease-deficient DNA polymerase with the target DNA as the template and the 3'-end of P1 as the primer, all under conditions that discriminate between a mismatched and a matched 3'-end. Following said limited DNA synthesis, perhaps for as many as 40 to 50 residues, but at least about 40 residues, the target DNA is removed by altering conditions so as to promote such removal. The extension of P1 remains because it is covalently attached to what had been the 3'-end of P1 but without the need for a ligation step. In a further embodiment of the invention, an intentionally placed mismatch may also occur at residue −3 of the ASO or P1 (i.e., third residue from the 3'-end), which mismatch may increase the sensitivity of the allele discrimination depending on the exonuclease-deficient DNA polymerase used.

In accordance with the invention disclosed herein, the P1 primer may be any type of oligonucleotide provided that it contains the appropriate allele-specific sequences useful in the methods of the invention and wherein the 3'-terminal nucleotide provides the desired match or mismatch for subsequent extension in the case of a match. In a preferred embodiment, such probe oligonucleotides contain a 3'-terminal phosphorothioate structure, which structures are resistant to exonuclease digestion. In addition, the hydrogen bond of such a derivative is weaker and thus enhances the chemical difference between matched and mismatched pairs. In another embodiment, the last two, preferably three, phosphodiester bonds are replaced by phosphorothioate derivatives. It should be noted that, which P1 probe, or P1 primer, extension occurs only when there is a match between the probe and the target, such a match may or may not be indicative of a wild-type or mutant allele present in the target DNA. Thus, depending on the inclinations of the user, the methods disclosed herein allow such match to indicate either a wild-type or mutant allele, depending on the sequence used in the ASO (or P1).

As shown in panel C of FIG. 1, a second primer (P2), called the amplification primer, containing the RCA platform, or amplification primer sequence, is annealed (i.e., hybridized) to the newly extended and immobilized DNA (although such procedure could work in solution or suspension). Amplification primer P2 is bifunctional, or bipolar, in that it possesses two functionalities separated by a stretch of thymidines (see, for example, SEQ ID NO: 27). In addition, P2 possesses a first segment, portion, fragment or sequence that is complementary to a segment, if not the entire sequence, of the extended portion of P1 (and therefore has a sequence highly homologous, if not identical, to the target DNA sequence previously used as the template for synthesis of the extended portion). In addition, amplification primer P2 comprises a second segment, portion, fragment or sequence, called the amplification primer sequence, located at the 3'-end opposite said first complementary sequence, which amplification primer sequence is complementary to a sequence present on single-stranded DNA circles, called amplification target circles (ATCs), such that when the latter are added to the mixture, said ATCs hybridize to the amplification primer sequence, the latter then serving as a primer for rolling circle amplification (RCA) using the amplification target circle DNA as template.

Following addition of ATCs to the reaction mixture, and addition of a DNA polymerase capable of carrying out rolling circle amplification, such as T7 DNA polymerase, the conditions are altered so as to promote said rolling circle amplification to produce a linear chain of DNA possessing repeated segments of sequences complementary to the sequence of the ATCs. Such RCA product is referred to as tandem sequence DNA (or TS-DNA). The RCA products, or TS-DNAs, are detected by standard procedures, for example, using labeled decorator oligonucleotides as probes or direct incorporation of labeled dNTPs. As shown in FIG. 1, Panels C and C', only extended primer (complementary to target DNA template on which it was synthesized and also complementary to said first segment of amplification primer P2) will give an RCA signal (i.e., give rise to TS-DNA product). The mutant DNA, causing a mismatch with the terminal 3'-residue of P1, fails to provide a template for extension of P1 by the mismatch sensitive polymerase enzyme used to extend P1 and thus there is no extended P1 portion to anneal to the subsequently added amplification primer P2. By way of non-limiting example, the exonuclease-deficient polymerase, T7 Sequenase, can discriminate a mismatched from a matched 3'-end by 400-fold. Alternatively, a separate exonuclease-deficient polymerase, Tth polymerase, can distinguish such mismatches by about 300-fold. Other DNA polymerases capable of distinguishing a matched from a mismatched pair and useful in practicing the methods of the present invention include Klenow polymerase (exo$^-$), Vent polymerase (exo$^-$), Deep Vent polymerase (exo$^-$), Pfu polymerase (exo$^-$), Taq polymerase, the Stoeffel fragment of Taq polymerase, Bst polymerase, Tts polymerase and ThermoSequenase, a list that is in no way intended to be limiting or exhaustive.

Figure 2:
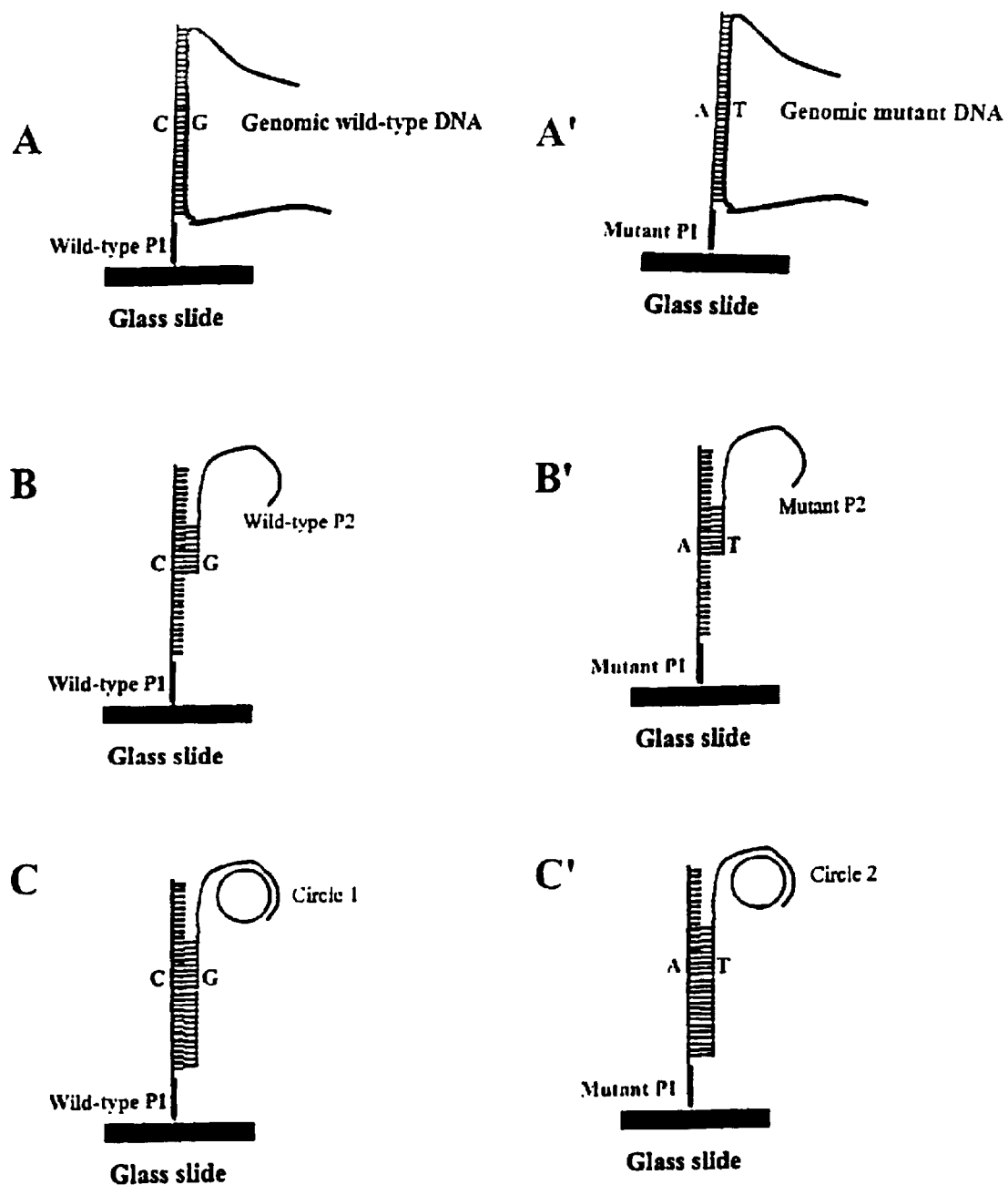
FIG. 2 shows an additional embodiment wherein wild-type and mutant target DNA is annealed to allele-specific P1 primers. The 3'-end of P1 is then extended (see panels A and A', respectively, for wild-type and mutant alleles) as described in FIG. 1 and the target DNA subsequently removed. A short allele-specific bifunctional, or bipolar, primer (P2) is then annealed to the newly synthesized extended DNA (panels B and B') and elongated again under conditions that discriminate a matched from a mismatched 3'-end (panels C and C'). The P2 primer that was not elongated during primer extension is washed away before an allele-specific circle (ATC) is annealed to P2. The allele-specific RCA products are then detected using labeled oligonucleotide detectors. P1 is immobilized on a glass slide but other substrates are usable within the claimed invention.

FIG. 2 shows a separate embodiment of the present invention wherein a second discrimination step is included that increases the specificity and allows simultaneous detection of wild-type and mutant alleles, as well as the presence of any number of different alleles. Here, an optionally immobilized oligonucleotide primer (P1), or ASO, attached to the solid support at its 5'-end, contains a 3'-terminal nucleotide complementary to one of the 4 possible nucleotide bases (A, T, G, or C, but only CG and AT pairs are shown in the figure, left and right, respectively) located at the residue of a genomic DNA (wild type or any one of a number of mutant alleles) to be tested for mutation (i.e., for a single nucleotide polymorphism or SNP). Following addition and annealing of target DNA (wild type or mutant), the latter again acts as template for primer extension of the P1 oligonucleotide probe. However, in this case the P1 oligonucleotides (or ASOs) available for binding the target DNA differ in their 3'-terminal residue (with 4 different kinds of P1—each with a different one of the four possible nucleotide bases at the 3'-terminus (and optionally an additional mismatch at residue −3) so that target DNA will bind to the P1 oligonucleotide probes. However, primer extension of the P1 probes, by exonuclease-deficient DNA polymerase, occurs only where there is no mismatch between the test residue of the target DNA and the 3'-terminal residue of the P1 probe. After primer extension (with the exonuclease-deficient DNA polymerase extending P1 only beginning at the matched ends) the target DNA is removed and bipolar amplification primers (P2) added, the latter again possessing a first sequence complementary to the extended portion P1' (the extended form of P1). At this point in the process of the invention, conditions are altered to promote a second round of primer extension, this time extension of the amplification primer P2 along P1 as template to form the extended products shown in FIG. 2, Panels C and C', for wild type and mutant alleles, respectively, again utilizing exonuclease-deficient DNA polymerase sensitive to a mismatch at the original 3'-terminal residue of P1 and the 3'-terminal residue of P2. Amplification primer P2 also contains either a match or a mismatch with the original 3'-terminal residue of probe P1 and will thereby be extended only if there is no mismatch at this point. Following extension of matched P2 oligonucleotides, conditions are adjusted so that non-extended P2 oligonucleotides are removed (facilitated by a lower degree of hybridization leading to weaker overall binding) and only extended P2 oligonucleotides have sufficient hybridization binding to P1 so as to remain attached. Thereafter, ATCs are added and RCA carried out as previously described for FIG. 1 except that, because different P2 oligonucleotides may be present and thereby amplified, ATCs with different sequences may be employed. The products produced by subsequent RCA in this case are different TS-DNAs (i.e., TS-DNAs with different sequences reflecting the different sequences of the complementary ATCs which in turn reflect the different amplification primer sequences of the amplification primers (P2) and whose relative concentration will reflect the degree of primer extension of the original P1 and P2 oligonucleotide probes, respectively).

In this latter embodiment amplification primer P2 is a bipolar primer that possesses two 3'-ends separated by a carbon linker (see, for example, SEQ ID NO: 34 and 35). Thus, in practicing the processes of the present invention, two different P2 primers are available, one for each of two separate embodiments, although other possibilities are also contemplated. Both types of P2 primer exemplified by the figures and examples disclosed herein are bifunctional in that one end comprises an RCA platform while the other end facilitates target recognition. For example, the P2 primer depicted in FIG. 1 has normal polarity (i.e., 5'- to 3'-) with the segments separated by a run of thymidines (or T's) as exemplified by the sequences of SEQ ID NO: 27 and 28. A second type of P2 useful in the present invention, as illustrated by the process shown in FIG. 2, has reverse polarity 3'-5'-3' and the segments are separated by a carbon linker that can be anywhere from about 6 to about 18 carbons in length, for example, as methylene groups, for which the chemistry and routes of synthesis are well known to those of skill in the art. In addition, such structures are readily available from numerous commercial sources. By way of example only, for use in detecting mutations associated with the G542X locus (as depicted in FIG. 2), such P2 primers might have the following sequences:

GTTCTTGATATAACAGAAAGTTTTTTTATGATCACAGCTGAGGATAGGACAT SEQ ID NO: 34

GCGA transformed into a bipolar primer having the structure

3'-GTTCTTGATATAACAGAAAGTTTT-5'-(CH2)n    SEQ ID NO: 35

-5'-TTTTATGATCACAGCTGAGGATAGGACATGCGA-3' with n = 6 to 18 and

TTTCTTGATATAACAGAAAGTTTTTTTCTTGTACATGTCTCAGTAGCTCGTC

AGT transformed into a bipolar primer having the structure

3'-TTTCTTGATATAACAGAAAGTTTT-5'- (CH2)n

-5'-TTTTCTTGTACATGTCTCAGTAGCTCGTCAGT-3' with n = 6 to 18

As used in such a procedure, a bipolar reverse primer (where P2 is 3'-5'-3' or a different bifunctional primer as disclosed herein) containing a short target-specific sequence (about 15–17 nucleotides long, with low $T_m$ (melting temperature)) terminating at an allele-specific 3'-end and the RCA platform are annealed to the newly synthesized (i.e., extended) and immobilized DNA. To anchor the P2 primer to the immobilized DNA, primer extension is again performed under conditions that discriminate a mismatched from a matched 3'-end. Before RCA is performed, unextended P2 primer is removed by high stringency washes taking advantage of the low $T_m$. This ensures that only allele-specific RCA product will be detected. Multiplexing is accomplished by using allele-specific circles. Using a second discrimination step with either the T7 Sequenase or Tth polymerase increases allele-specificity to over 10,000 fold.

An allele specific oligonucleotide is a linear single-stranded DNA molecule, generally containing between 50 to 1000 nucleotides, preferably between about 60 to 150 nucleotides, and most preferably between about 70 to 100 nucleotides. The allele-specific oligonucleotide (probe P1) has a 5'-amino group and a 3'-hydroxyl group. This allows the 5'-end to be optionally affixed to a solid support, such as the glass slide shown in the embodiments of FIGS. 1 and 2. Portions of the allele-specific oligonucleotide (probe P1) have specific functions making the allele-specific oligonucleotide (probe P1) useful for annealing either to target DNA or to an amplification probe (P2) so as to facilitate eventual rolling circle amplification (RCA). These portions are referred to as the target probe portion (located at the 3'-end), which is complementary to the target DNA, with the possible exception of the 3'-terminal residue of P1, either wild type or mutant (i.e., to different alleles of the gene or genes to be tested) as well as the attachment portion, located at the 5'-end, which serves to attach the probe to a solid support. The target probe portion is a required element of an allele-specific oligonucleotide (ASO, P1). Generally, an allele-specific oligonucleotide (the P1 of FIGS. 1 and 2) is a single-stranded, linear DNA molecule comprising, from 5' end to 3' end, a 5'-amino group, a target probe portion (or segment, or fragment, or sequence), terminating in a nucleotide residue that may or may not match the corresponding residue on the target DNA when the target probe portion of P1 is hybridized to the target DNA, and a 3' hydroxyl group, with an optional mismatch residue at position −3 (the third residue upstream of the 3'-OH)—compare, for example, SEQ ID NOs: 1–4). Other portions of the allele-specific oligonucleotide can be arbitrarily chosen as to sequence, especially where such selected facilitates binding to a solid support or substrate. It is preferred that allele-specific oligonucleotides (probe P1) do not have any sequences that are self-complementary, with this condition being met if there are no complementary regions greater than six nucleotides long without a mismatch.

The amplification probe (P2), with one segment annealed to the ASO (P1) and the other annealed to an amplification target circle (ATC) serves as a primer for replication of the ATC after the latter is annealed to said P2 amplification probe. In the embodiment of FIG. 2, said amplification probe, for example, SEQ ID NO: 13, is itself extended on a template formed from P1 and, after annealing of the ATC, and addition of a suitable DNA polymerase, which may or may not be the DNA polymerase used for mismatch detection and extension, gives rise to a long DNA molecule (called TS-DNA or tandem-sequence DNA) containing multiple repeats of sequences complementary to the open circle probe.

As already described, TS-DNA contains sequences complementary to the amplification target circles (ATCs), which contain a segment complementary to the amplification primer segment of the amplification primer oligonucleotides P2, the latter sequence also acting as a primer for amplification of the ATCs. These sequences in the TS-DNA are referred to as primer sequences (and match the sequence of the rolling circle replication primer or amplification primer P2) and the selectable complementary sequences (which match in complementary fashion the ATC segment that is not complementary to amplification primer sequence of P2 and which sequences may be arbitrarily chosen). This latter selectable sequence may comprise various sequences useful in detection of the tandem sequence DNA and which may include such sequences as detection tags, secondary target sequences, address tags, and promoter sequences.

A particularly preferred embodiment is an allele-specific oligonucleotide of 70 to 100 nucleotides including a target sequence probe of about 10 to 20 nucleotides at or near the 3'-end.

In accordance with the present invention, the sequence containing potential allelic variations to be detected forms the target oligonucleotide, or target sequence, or target DNA, and contains a sequence complementary to a portion of the allele-specific oligonucleotide (P1) of the Figures. As used herein, the term "target polynucleotide" or "target DNA" or "target sequence" includes multiple separate polynucleotide strands that contain one or more allelic differences over the probe oligonucleotide (P1) and which can be separately amplified and/or detected. A target polynucleotide may be a single molecule of double-stranded or single-stranded polynucleotide, such as a length of genomic DNA, cDNA or viral genome including, possibly, RNA, or a mixture of polynucleotide fragments, such as genomic DNA fragments or a mixture of viral and somatic polynucleotide fragments from an infected sample. Typically, a target polynucleotide or target DNA starts as a double-stranded DNA which is denatured, e.g., by heating, to form single-stranded target molecules capable of hybridizing with primers and/or oligonucleotide probes represented by P1 in the Figures herein.

In general, the term "oligonucleotide" as used herein includes linear oligomers of natural or modified monomers or linkages, comprised of including deoxyribonucleotides, capable of specifically binding to a target polynucleotide by way of a regular pattern of monomer-to-monomer interactions, such as Watson-Crick type complementary base pairing, and capable of being ligated to another oligonucleotide in a template-driven reaction. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "GATTACA," it will be understood that the nucleotides are in 5' to 3' direction from left to right and that "A" denotes deoxyadenosine, "C" denotes deoxycytidine, "G" denotes deoxyguanosine, and "T" denotes thymidine, unless otherwise noted. The term "polynucleotide" as used herein usually means a linear oligomer of nucleotides or analogs thereof, including deoxyribonucleotides, ribonucleotides, and the like, from a few tens of units in length to perhaps a hundred or more units long, possibly longer.

When used in referring to oligonucleotide probes of the present invention, such as P1 or P2, including primers, the term "plurality" is construed as sufficiently broad to encompass sets of two or more oligonucleotide probes where there may be a single "common" oligonucleotide probe that is usually specific for a non-variable region of a target polynucleotide and one or more "wild-type" and/or "mutant" oligonucleotide probes that are usually specific for a region of a target polynucleotide that contains allelic or mutational variants in sequence. In general, such probes will have varying nucleotides at one nucleotide location only, but more than one difference is possible within the methods disclosed herein.

The term "amplification primer", as used herein, refers to an oligonucleotide that acts to initiate synthesis of a complementary DNA strand when put into conditions where synthesis of a primer extension product is induced, i.e., in the presence of nucleotide triphosphates and a polymerization-inducing agent, such as a DNA-dependent DNA polymerase, including an exonuclease deficient DNA-dependent DNA polymerase, and also including RNA polymerases, such conditions including a suitable temperature, pH, metal concentration, and salt concentration. For purposes of the present disclosure, P2 is an amplification primer.

An important aspect of the methods of the present invention is the use of an exonuclease-deficient polymerase, such as a DNA polymerase, for extension of the primer strand formed by the original allele-specific oligonucleotide (P1) and using the target DNA as a template for extending this allele-specific primer in a manner such that no extension occurs if there is a mismatch at the terminal 3'-end of the allele-specific primer (P1). Use of such enzymes obviates the need to carry out a ligation step while simultaneously serving to detect the presence of a mismatch in the sequences of the target DNA versus the allele-specific oligonucleotide probe (P1). Such enzymes are readily available for use in the methods of the invention. Thus, such enzymes as T7 Sequenase and Tth polymerase are useful in the methods disclosed herein. In addition, other such enzymes have been constructed to have the requisite properties. For example, Foxall et al (U.S. Pat. No. 5,985,569) disclose the use of an exonuclease deficient polymerase to amplify selected segments of microbial DNA sequences and related mismatches to primer melting temperatures. Mamone (U.S. Pat. No. 5,827,716) discloses a procedure for constructing a modified pol 11 type DNA polymerase that is an exonuclease deficient polymerase. To be useful within the methods of the invention, such an enzyme should be able to detect a mismatched from a matched 3'-base by at least 2 orders of magnitude, or about 100 times, preferably at least about 200 fold, and most preferably at least about 400 fold. In addition, the assays provided herein are greatly simplified and facilitated by polymerases that catalyze both primer extension and RCA. For the exonuclease-deficient polymerase already mentioned, T7 Sequenase, can discriminate a mismatched from a matched 3'-end by 400-fold. Alternatively, the separate exonuclease-deficient polymerase, Tth polymerase, can distinguish such mismatches by about 300-fold.

The methods of the present invention further provide optimal conditions for primer extension and subsequent allele discrimination. Such conditions are readily determined, however, using a model ATC DNA sequence, perhaps about 100 nucleotides in length, and finding optimal conditions by comparing genomic and cloned DNA.

After primer extension is complete, conditions within the mixture are adjusted to remove the heretofore hybridized target DNA and then washing said Target away. The resulting extended single stranded polynucleotide is then mixed with a second oligonucleotide (P2) containing a first sequence complementary to the extended primer and a second sequence complementary to a selected sequence of an amplification target circle (ATC). After addition of such a target circle, and hybridization of the ATC to the primer (P2), the latter then acts as a primer for subsequent rounds of DNA replication using the ATC as template. The single stranded DNA produced from such replication of the ATC is referred to as "tandem sequence DNA," or TS-DNA, because the same sequences (complementary to the sequence of the ATC) are replicated repeatedly, the sequence identity thereof being determined by the sequences of the ATC.

Thus, in accordance with the present invention an amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. Ligated open circle probes are a type of ATC, and as used herein the term amplification target circle includes ligated open circle probes.

As described, an amplification target circle, when replicated, gives rise to a long DNA molecule containing multiple repeats of sequences complementary to the amplification target circle. This TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer that was complementary to the ATC), detection sequences, secondary target sequences, address tags, and promoter sequences. Amplification target circles are useful as tags for specific binding molecules.

As disclosed herein, there is provided a second oligonucleotide probe (P2) that acts as an amplification primer to facilitate rolling circle replication. An amplification primer, or rolling circle replication primer, is an oligonucleotide having a sequence complementary to most or all of the extended portion of the allele-specific oligonucleotide (probe P1) and an amplification primer portion complementary to a segment of the amplification target circle (ATC), shown as the single-stranded DNA circle in panel C or FIGS. 1 and 2. The amplification primer portion of an amplification primer (such as P2) and the complementary portion of the ATC can have any desired sequence so long as they are complementary to each other. In general, the sequence of an amplification primer (P2) is chosen such that it is not significantly complementary to any portion of the allele-specific oligonucleotide (probe P1) other than the portion of P1 that is extended by the exonuclease-deficient DNA polymerase to form an extended probe (herein denoted P1' and formed by extension of P1 using the target DNA as template) and likewise is complementary only to the portion of the ATC to which it is intended to bind. The complementary portion of an amplification primer can be any length that supports specific and stable hybridization between the primer and the primer complement portion. Generally this is 10 to 35 nucleotides long, but is preferably 16 to 20 nucleotides long.

It is also preferred that rolling circle replication primers also contain an additional sequence at the 3'-end directed away from the solid support of the Figures and which is not complementary to any part of the allele-specific oligonucleotide (probe P1) nor to the ATC. This segment is referred to as the non-complementary segment, or spacer, and is normally situated between the segment complementary to P1 and the segment complementary to the ATC. The non-complementary segment, or spacer, of the amplification primer generally serves to facilitate strand displacement during RCA. The non-complementary portion of the amplification primer (P2) may be any length, but is generally 1 to 100 nucleotides long, and preferably at least 5 to 10 nucleotides long. The amplification primer, or rolling circle replication primer, may also include modified nucleotides to make it resistant to exonuclease digestion where DNA polymerases with exonuclease-activity are employed for RCA. For example, the primer can have three or four phosphorothioate linkages between nucleotides at the 5'- and 3'- ends of the primer sequence.

While the methods disclosed herein work in solution, or in a suspension, they are easily and advantageously adapted to work on a solid support. In a specific embodiment, the methods of the invention work well when the allele-specific probe is attached to a solid support, most preferably at the end opposite that containing the potential mismatched nucleotide. Such solid-state substrates for use in methods disclosed herein include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide. The most preferred form of a glass slide is a microarray of P1 primer oligonucleotides.

Thus, in accordance with the invention disclosed herein, there is provided a means of utilizing primer extension, such as in situ primer extension, or "PRINS," coupled with RCA to detect mutations (i.e., allelic differences) as an advantageous alternative to the bipartite oligonucleotide ligation methods already available. In doing so, a bifunctional oligonucleotide containing the RCA primer in an allele-specific manner is anchored to a target gene, or other DNA sequence, such as from a genome, so that positional information contained therein is preserved.

Many alleles of a large number of genes have been sequenced for research purposes and these sequences are stored in the EMBL databank (for Europe) and in Genbank (USA), both of which are accessible to subscribers. On the basis of these sequences, many sequences can be examined for potential single-nucleotide polymorphisms and thereby used to identify different alleles that are susceptible to examination using the methods disclosed herein. Most genes and systems of genes contain regions of sequences which are subject to different degrees of sequence variability (i.e., mutation). Depending on the gene system, such variability may have been extensively studied and is available for further analysis by the methods described herein. Thus, the presence of usable sequences for the methods according to the present invention can be detected by more detailed analysis of Genbank and EMBL submissions, supplemented by self-determined sequences.

Amplification primers (such as P2) and oligonucleotide probes (such as P1) are readily synthesized by standard techniques, e.g., solid phase synthesis via phosphoramidate chemistry, as disclosed in U.S. Pat. Nos. 4,458,066 and 4,415,732 and other references, the literature on which is extensive and given to even the most routine search. Likewise, the amplification primers and oligonucleotide probes useful in the methods of the present invention may are conveniently derivatized with reactive groups, e.g. for attaching labels, using conventional chemistries. [See, for example, Eckstein, editor, Oligonucleotides and Analogues: A Practical Approach (IRL Press, Oxford, 1991).

The amplification target circles useful in the methods of the present invention may conveniently have incorporated into them specifically selected sequences, part of the non-complementary sequences, that provide a ready means for detecting the tandem sequence products produced by rolling circle amplification using P2 as primer. The tandem sequence products can thereby be detected by almost any means imaginable, including the use of distinct labels detectable by spectroscopic, photochemical, biochemical, immunochemical or radiochemical means. Detection may also be achieved by using a nucleic acid hybridization assay, e.g. as described in Urdea et al, U.S. Pat. No. 5,124,246, or like techniques that can be employed as sensitive probes of the nucleotide sequences that are repeated within the tandem sequence products of RCA.

In a preferred embodiment, an oligonucleotide probe used to measure the presence of complementary sequences repeated within the tandem sequence product contains a fluorescent label that is readily detected since the product, which is an extension of the amplification primer (P2) is affixed to P1 and thereby to the solid support. Thus, the tandem sequence DNA product can be readily separated from the reaction mixture and the presence of one or more sequences within the tandem repeats readily measured with sensitive probes attached to such labels. Among the more common such fluorescent labels available for use include 5-carboxyfluorescein (5-FAM), 6-carboxyfluorescein (6-FAM), 2',7'-dimethoxy-4',5'-dichloro-6-carboxyfluorescein (JOE), N,N,N', N'-tetramethyl-6-carboxy rhodamine (TAMRA), 6-carboxy-X-rhodamine (ROX), 4,7,2',4',5 ',7'-hexachloro-6-carboxy-fluorescein (TET-1), 4,7,2',4',5',7'-hexachloro-5-carboxy-fluorescein (HEX-2), 2',4',5',7'-tetrachloro-5-carboxyfluorescein (ZOE), 4,7,2',7'-tetrachloro-6-carboxy-fluorescein (TET-1), 1',2',7', 8'-dibenzo-4,7-dichloro-5-carboxyfluorescein (NAN-2), and 1',2',7',8'-dibenzo-4,7-dichloro-6-carboxyfluorescein, Texas-Red, Cy3, and Cy5 dyes.

Preferably, oligonucleotide probes are fluorescently labeled by linking a fluorescent molecule to a terminal portion of the probe sufficiently distant from the portion complementary to the sequence to be measured in the tandem sequence product so as not to adversely affect hybridization, which may already be carried out under stringent conditions. In order to facilitate detection in a multiplex assay (see below), copies of different reporter probes are labeled with different fluorescent labels. Guidance for selecting appropriate fluorescent labels can be found in Smith et al. (1987) Meth. Enzymol. 155:260-301, Karger et al. (1991) Nucl. Acids Res. 19:4955–4962, Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318,846 to Khanna et al. and Lee et al. (1989) Cytometry 10:151–164, and 6-FAM, JOE, TAMRA, ROX, HEX-1, HEX-2, ZOE, TET-1 or NAN-2, as described above, and the like. Most preferably, when a plurality of fluorescent dyes are employed, they are spectrally resolvable, meaning that they give quantum yields, emission bandwidths, and emission maxima that permit electrophoretically separated polynucleotides labeled therewith to be readily detected despite substantial overlap of the concentration bands of the separated polynucleotides.

By linking appropriate sequences to the RCA product, such as by incorporation of sequences within the amplification probe (P2) that can readily be detected by other oligonucleotides capable of binding thereto in a sequence specific manner, a number of different agents, such as the fluorescent agents mention above, can be induced to bind to specific sequences within the TS-DNA if those sequences are present. For example, if it is desired to determine if a specific sequence is present in the TS-DNA (i.e., whether a given probe was extended or not in response to a match with the target DNA or allele specific probe) this sequence can be hybridized to a probe that is itself attached to some other structure, such as a fluorescent label or even a protein that reacts with an antibody useful in detecting the presence of the protein and thereby the presence of the target sequence). Such agents are referred to in the art as reporter binding agents.

As used herein, and in the art generally, a reporter binding agent is a specific binding molecule or other molecular structure attached, coupled or, otherwise tethered in some manner, to an oligonucleotide. The specific binding molecule is commonly referred to as the affinity portion of the reporter binding agent and the oligonucleotide is the oligonucleotide portion of said reporter binding agent. Said specific binding molecule is a molecule that interacts in a specific manner with a particular molecule or moiety. For example, antibodies and other molecules with specific affinities are examples of such specific binding molecules and can readily be attached to an oligonucleotide to form the affinity portion of a reporter binding molecule. By attaching an amplification target circle or coupling a target sequence to such specific binding molecules, binding of said specific binding molecule to its specific target can be detected by amplifying the ATC or target sequence with rolling circle amplification. This additional amplification allows sensitive detection of even a very small number of bound specific binding molecules.

In one embodiment, the oligonucleotide present as part of the reporter binding agent comprises a sequence, called the probe sequence, that can act as a probe for selected sequences present on the TS-DNA. This probe sequence can be arbitrarily chosen. In a multiplex assay using multiple reporter binding agents, it is preferred that the probe sequence for each reporter binding agent be substantially different to limit the possibility of non-specific target detection. Alternatively, depending on the system being used, the purpose of the experiment or process, and types of nucleotide sequences being employed, especially where certain multiplexing assays are being carried out, that probe sequences have related sequences.

The oligonucleotide portion can be coupled to the affinity portion by any of a number of methods well known in the art for linking oligonucleotides to other types of molecules. (see, for example, Hendrickson et al., *Nucleic Acids Res.*, 23(3):522-529 (1995), which describes a suitable method for coupling oligonucleotides to antibodies).

In another embodiment, the oligonucleotide portion of a reporter binding agent can itself include an ATC to serve as a template for RCA. Thus, in a multiplex assay using multiple reporter binding agents, it may be desirable and advantageous to employ ATCs that themselves incorporate address tags and sequences independently identifiable using separate reporter binding agents. These latter commonly also comprise the oligonucleotide portion typical of reporter binding agents useful in the methods of the invention but such oligonucleotide portions of said reporter binding agents should advantageously be substantially different so as to facilitate unique detection of each reporter binding agent. Of course, the same primer complement portion will normally be employed in all of the ATCs used in such a multiplex assay. The ATC is most conveniently one that is covalently, or otherwise, attached to said specific binding molecule by means known in the art, such as by looping the ATC around a tether loop and thereby allowing the ATC to rotate freely during rolling circle replication while remaining coupled to the affinity portion, for example, the antibody portion of the reporter binding agent. Such tethering materials can include polymers or other common substances used in the molecular biological arts for accomplishing the tethering of molecules. Polymers are the preferred material for tether loops and such polymers can include oligonucleotides as well as oligopeptides. Thus, oligonucleotides can be coupled to specific binding molecules using known techniques. For example, Hendrickson et al. (1995), describes a suitable method for coupling oligonucleotides to antibodies (although such methods are generally useful for coupling oligonucleotides to proteins of all kinds), and Lizardi (U.S. Pat. No. 5,854,033 containing a general discussion of such technology. The ends of such tether loops can also be advantageously coupled to any specific binding molecule using functional groups that can be readily derivatized with suitable activating groups. For methods employing proteins and similar molecules, some useful methods are described in Protein immobilization: fundamentals and applications Richard F. Taylor, ed. (M. Dekker, New York, 1991). For use of antibodies as the affinity portion, such antibodies may be prepared by means well known in the art and may include polyclonal and monoclonal antibodies, as well as recombinant and synthetic antibodies well known in the art.

As is clear by the foregoing, various methods of detection, and levels of detection, are afforded by the labeling methods disclosed herein. Thus, the above labeling methods can operate by incorporating labeled moieties, such as fluorescent, including nucleotides, biotinylated nucleotides, digoxygenin-containing nucleotides, or bromodeoxyuridine, during rolling circle replication in RCA. For example, one may incorporate cyanine dye UTP analogs (Yu et al. (1994)) at a frequency of about 4 analogs for every 100 nucleotides.

A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif), followed by binding of the biotin moieties with Streptavidin-Peroxidase (Life Sciences, Inc.) (see, for example, Example 1, below)), and development of fluorescence with Fluorescein-tyramide (DuPont de Nemours & Co., Medical Products Dept.).

Additional labeling methods can be employed wherein suitable molecular probes are used to detect amplified DNA. For example, an ATC may be designed to contain several repeats of a known arbitrary sequence, referred to as detection tags. A secondary hybridization step, as already described herein, can be used to bind the detection probes described above to such detection tags. The detection probes may be labeled as described above with enzymes, fluorescent moieties, radioactive isotopes and the like. By combining fluorescent moieties and detection tags one can theoretically obtain hundreds, if not thousands, of fluorescent signals for every open circle probe repeat in the TS-DNA.

Rolling circle amplification is a highly useful means of amplification because, inter alia, it is readily given to multiplexing through the use of different open circle probes, each set of such probes carrying different probe sequences designed for binding to unique complementary targets. Because the primer complement portion remains constant the same primer for rolling circle replication can be used regardless of the identity of the target. Said amplification primers may, however, differ in the portion that is complementary to the extended ASO (or P1') and thus only some of these primers may wind up being replicated after addition of ATCs and DNA polymerase. Because only those ASOs with a matched pair of residues will be extended and bind to the primer and give rise to TS-DNA, the particular TS-DNA produced, and the relative quantities of such TS-DNAs, will depend on the relative amounts of matched and mismatched target/probe pairs. Alternatively, the ATC-complementary portions of the amplification primers (P2) can themselves be different so as to hybridize with different kinds of ATCs, thereby serving as a separate means of detection, thus amplifying the detection results. The relative amounts of such products are then quantitated using any of the methods described herein with any of the reporter binding agents already described above.

The present invention is also directed to a method for diagnosing a disease characterized by a genetic mutation comprising:

(a) obtaining a sample of a mutated gene sequence from an organism afflicted with said disease; and (b) carrying out the process of claim 1 wherein at least a portion of said mutated gene sequence is used as either the target polynucleotide or the allele specific oligonucleotide.

In carrying out the methods of the invention, a sample is provided which includes DNA containing target nucleotide sequences (i.e., a mutated gene sequence is used as the target polynucleotide) either derived from an organism or wholly synthetic in origin. Such organism, of course, may typically be an animal, including a human. Thus, the DNA useful, especially as target DNA, in the processes disclosed herein may be genomic DNA, or DNA derived from genomic DNA, or wholly synthetic DNA, wherein said DNA is derived from a human, or a non-human organism, such as some other animal, especially a mammal, or even from a non-animal source, such as a mutation in a plant or other vegetative structure. Such DNA sample may also include a mixture of any of the DNAs recited herein, wherein said mixture is comprised of samples from at least two different sources, or comprises different DNA segments derived from the same source, such as DNA derived from two different cells or tissues of the same organism, such as a human.

By way of example, chromosomal DNA of an individual who is being tested or screened is obtained from a cell sample from that individual (most commonly, the source is human but need not be since any animal can be tested using the methods of the present invention). Cell samples can be obtained from a variety of tissues depending on the age and condition of the individual. For example, cell samples may be obtained from peripheral blood using well known techniques. In fetal testing, a sample is preferably obtained by amniocentesis or chorionic villi sampling. Other sources of DNA include semen, buccal cells, and cells found in the feces. Preferably, DNA is extracted from the sample using standard procedures, e.g., phenol:chloroform extraction as described by Maniatis et al., referred to above, and Higuchi (May 1989) PCR Applications, Issue 2 (Perkin Elmer-Cetus Users Bulletin). Cell samples for fetal testing can also be obtained from maternal peripheral blood using fluorescence-activated cell sorting, as described, e.g., by Iverson et al. (1981) *Prenatal Diagnosis*, 9:31-48.

In light of the foregoing, it is clear that the present invention relates to diagnosis of diseases caused by, induced by, or related to a mutation in at least one gene or other sequence of DNA, such as a promoter region or some type of enhancer region located either cis or trans to a gene whose expression is affected by such mutation.

Diseases readily diagnosed by the methods of the present invention include, but are in no way limited to, diseases selected from the group consisting of Parlinson's disease, Duchenne muscular dystrophy, Niemann-Pick disease, polyposis, neurofibromatosis, polycystic kidney disease, Tay-Sachs disease, xeroderma pigmentosa, ataxia-telangiectasia, Huntington disease, Li-Fraumeni syndrome, beta-thalassemia, sickle cell anemia, hemoglobin C disease, hemophilia, acute intermittent porphyria, cystic fibrosis, diabetes, obesity and cancer, as well as other types of cancer wherein a genetic mutation is involved. Such cancers include, but are in no way limited to, cancers selected from the group consisting of leukemia, lymphoma, melanoma, neuroblastoma, retinoblastoma, rhabdomyosarcoma, Ewing sarcoma, head and neck cancer, skin cancer, brain cancer, esophageal cancer, stomach cancer, lung cancer, breast cancer, colon cancer, ovarian cancer, testicular cancer and prostate cancer.

The present invention further relates to kits for carrying out the methods of the invention. Preferably, such kits include (a) a plurality of oligonucleotide probes, each oligonucleotide probe of the plurality being capable of hybridizing to one or more target polynucleotides that may or may not possess a mismatch with respect to a terminal residue of the oligonucleotide probes; (b) a sample of an exonuclease deficient DNA polymerase; (c) plurality of amplification primers, each said primer being capable of hybridizing to an elongated segment of said oligonucleotide probe as well as comprising a primer sequence complementary to a sequence on an amplification target circle (ATC) for use in rolling circle amplification; (d) a sample of amplification target circles (ATC), essentially single stranded DNA circles, comprising a sequence of 10 to 20, even 30, nucleotides in length, which sequence is complementary to a sequence of the amplification primers of part (c) and which ATCs act as templates for rolling circle amplification (RCA); (e) a sample of a DNA polymerase capable of carrying out rounds of rolling circle amplification; and (f) a means for detecting the products of rolling circle amplification, including, but not limited to, various labeling reagents and address probes.

In carrying out the rolling circle replication of the amplification primers disclosed according to the invention, a wide variety of DNA polymerases are available for use provided only that they meet certain criteria. DNA polymerases useful in the rolling circle replication phase for detecting the presence of different alleles must have the capacity to perform rolling circle replication of primed single-stranded circles. Such polymerases are often referred to as RCA polymerases. For rolling circle replication, it is preferred that a DNA polymerase be capable of displacing the strand complementary to the template strand (the latter being the ATC), termed strand displacement, and lack a 5' to 3' exonuclease activity. Strand displacement is necessary to result in synthesis of multiple tandem copies of the amplification target circle or ATC. A 5' to 3' exonuclease activity, if present, might result in the destruction of the synthesized strand. It is also preferred that DNA polymerases for use in the methods disclosed herein are highly processive and the suitability of a DNA polymerase for use in the methods of the present invention should be tested in vitro for its ability to carry out RCA. Preferred rolling circle DNA polymerases are bacteriophage φ29 DNA polymerase (U.S. Pat. Nos. 5,198,543 and 5,001,050), phage M2 DNA polymerase (Matsumoto et al., *Gene* 84:247 (1989)), phage φ-PRD1 DNA polymerase (Jung et al., *Proc. Natl. Acad. Sci. USA* 84:8287 (1987)), VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219(2):267–276 (1994)), T4 DNA polymerase, *E. coli* DNA polymerase III holoenzyme (Kaboord and Benkovic, *Curr. Biol.* 5:149–157 (1995)), and T7 DNA polymerase, with φ29 and T7 DNA polymerase being especially preferred. Strand displacement can be facilitated through the use of a strand displacement factor, such as a helicase enzyme. For the most part, any DNA polymerase that can perform rolling circle replication in the presence of a strand displacement factor should be considered suitable for use in the disclosed method (some such DNA polymerases may require such factors for RCA). Strand displacement factors useful in RCA include BMRF1 polymerase accessory subunit (Tsurumi et al., *J. Virology* 67(12):7648–7653 (1993)), adenovirus DNA-binding protein (Zijderveld and van der Vliet, *J. Virology* 68(2): 1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22): 10665–10669 (1994)), Escherichia coil single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)). The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in the examples provided in Lizardi, U.S. Pat. No. 5,854,033, especially Example 1 thereof.

In a separate embodiment of the invention, it is possibly to detect multiple single nucleotide polymorphisms (i.e., multiple alleles) simultaneously through the process of multiplexing. Thus, at least 4 different allele-specific oligonucleotides (P1) can be employed to detect any one of 4 possible point mutations at the given site on the target DNA.

Each such allele-specific oligonucleotide would possess a different 3'-terminal nucleotide residue (for example, using the method of FIG. 2).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting example. In applying the disclosure of these examples, it should be kept clearly in mind that other and different embodiments of the methods disclosed according to the present invention will no doubt suggest themselves to those of skill in the relevant art.

EXAMPLE 1

For this run, the target sequence is the CFTR G542X locus characteristic of a mutation in cystic fibrosis. For this locus, rolling circle amplification had already been shown to work using the bipartite oligonucleotide ligation method (See: Lizardi et al, *Nature Genetics*, 19, 225–232 (1998)) and this process was able to discriminate mutant alleles. The target sequence is 46 nucleotides in length. For this example, both wild-type and mutant allele targets are utilized as template for primer extension, each template being 96 nucleotides in length.

Here, target-specific oligonucleotides (allele-specific oligonucleotides or ASOs, the P1 of FIG. 1) of length 23 nucleotides long and complementary to the target sequence of the cystic fibrosis G542X locus is utilized along with the T7 Sequenase as exonuclease-deficient DNA polymerase.

P1 primers useful in this example are:

Wild-type: C at 3'-end with even numbered primers containing A at −3:

1. 5'-CTCAGTGTGATTCCACCTTCTCC-3'  SEQ ID NO:1

2. 5'-CTCAGTGTGATTCCACCTTCACC-3'  SEQ ID NO:2

Mutant: A at 3'-end with even numbered primers containing A at −3:

3. 5'-CTCAGTGTGATTCCACCTTCTCA-3'  SEQ ID NO:3

4. 5'-CTCAGTGTGATTCCACCTTCACA-3'  SEQ ID NO:4

The primer (P1) used for the extension may optionally have an additional mismatch at the −3 position as a means of increasing discrimination. Primer extension is readily followed using a labeled primer and denaturing polyacrylamide gel electrophoresis.

Successful discrimination was defined on the basis of the ability of the primer extension process to give at least a 100-fold discrimination of mutant versus wild-type alleles.

Here, the target sequence comprises a 96 nucleotide synthetic oligonucleotide comprising either a 46 nucleotide wild-type or mutant human CFTR G542X locus sequence.

SEQ ID NO:5

Wild-type:

5'-pGACGAGTCAG AATCAGAGAA AGACAATATA GTTCTTGGAG

AAGGTGGAAT CACACTGAGC CCTATAGTGA GTCGTATTAA

ACTAAAGCTG AGACAT-3'

SEQ ID NO:6

Mutant:

5'-pGACGAGTCAG AATCAGAGAA AGACAATATA GTTCTTTGAG

AAGGTGGAAT CACACTGAGC CCTATAGTGA GTCGTATTAA

ACTAAAGCTG AGACAT-3'

In general, the synthetic targets each are 96 nucleotides in length, and primers are permitted to anneal at a temperature below the melting temperature ($T_m$). Additionally, templates are in excess over primers to avoid overloading and decrease non-specific priming. However, optimal conditions depend on the identity of the sequences, primers and targets and therefore must always be determined empirically. Primer extension is initiated by addition of the exonuclease-deficient DNA polymerase, all four deoxynucleoside triphosphates, and $Mg^{++}$. Reaction is most advantageously carried out at the maximum temperature permitted by the particular enzyme used.

Also optionally added to the reaction mixture are single-stranded binding proteins, which can facilitate prevention of primer extension of the mismatched base by recognizing and binding thereto. Proteins useful for such binding are *Escherichia coli* single-stranded binding (SSB) proteins and T4 gene 32 protein. These are advantageously titrated into the reaction mixture prior to addition of the DNA polymerase.

Radiolabeled oligonucleotide P1 (primer 1—here, SEQ ID NO: 1) at 0.1 $\mu$M was mixed with wild-type (SEQ ID NO: 5) or mutant (SEQ ID NO: 6) oligonucleotide target at 0.2 $\mu$M, increasing amounts of human heat denatured DNA, 40 mM Tris-HCl pH 7.5, 100 mM NaCl, 0.5 mM $MgCl_2$, 5mM DTT (dithiothreitol) 5 $\mu$M dATP, 5 $\mu$M dTTP, 5 $\mu$M dCTP, 5 $\mu$M dGTP, and allowed to anneal at 55° C. for 5 minutes. The 3'-end of the matched primer was then extended by adding 0.0033 Units T7 Sequenase and incubation for 5 minutes at 37° C. The reaction was stopped by adding urea loading dye and heating at 94° C. for 5 minutes. The 59 nucleotides in length extension product was analyzed on a 15% polyacrylamide-urea gel. The gel was dried and the band quantitated using a phosphoroimager. The quantitative data shows that T7 Sequenase discriminates better than 400:1 between wild-type and mutant template even in the presence of a high complexity DNA mixture.

EXAMPLE 2

For this experiment the target sequences are the CFTR G542X and M 1101K loci characteristic of naturally occurring mutations in cystic fibrosis. For the G542X locus, primer extension was already shown to discriminate wild-type from mutant in Example 1. For this example both wild-type and mutant allele oligonucleotide targets are utilized as templates, each template being 80 (G542X) or 68 (M1101K) nucleotides in length.

```
5'-TAATAGGACATCTCCAAGTTTGCAGAGAAAGACAATATAGTTCTTGGAG   SEQ ID NO: 7
   AAGGTGGAATCACACTGAGTGGAGGTCAACG-3'

5'-TAATAGGACATCTCCAAGTTTGCAGAGAAAGACAATATAGTTCTTTGAG   SEQ ID NO: 8
   AAGGTGGAATCACACTGAGTGGAGGTCAACG-3'

5'-CAACTGGTTCTTGTACCTGTCAACACTGCGCTGGTTCCAAATGAGAATA   SEQ ID NO: 9
   GAAATGATTTTTGTCATCT-3'

5'-CAACTGGTTCTTGTACCTGTCAACACTGCGCTGGTTCCAAAAGAGAATA   SEQ ID NO: 10
   GAAATGATTTTTGTCATCT-3'
```

Target-specific oligonucleotides (allele-specific oligonucleotides or ASOs, the P1 of FIG. 1) of variable length and containing a 3'-sequence complementary to the target sequence of the cystic fibrosis loci are utilized along with the T7 sequenase as exonuclease-deficient DNA polymerase.

P1 primers useful in this example are:

```
Wild-type G4542X: C at 3'-end
5'-NH2-(Carbon12)-TTTTTTTTTTTTTTTACCTCCACTCAGTGTGATTCCAC    SEQ ID NO: 11
   CTTCTCC-3'

5'-NH2-(Carbon12)-TTTTTTTTTTTTTTTTTTTTTTTTTAGTGTGATTCCAC    SEQ ID NO: 12
   CTTCTCC-3'

5'-NH2-(Carbon12)-TTTTTTTTTTTTTTTTTTTTTTTTTTTTTTGATTCCAC    SEQ ID NO: 13
   CTTCTCC-3'

5'-NH2-(Carbon12)-TTTTTTTTTTTTTTTTTTTTTTTTTTTTTTTTTTTCAC    SEQ ID NO: 14
   CTTCTCC-3'

Mutant G542X: A at 3'end
5'-NH2-(Carbon12)-TTTTTTTTTTTTTTTACCTCCACTCAGTGTGATTCCAC    SEQ ID NO: 15
   CTTCTCA-3'

5'-NH2-(Carbon12)-TTTTTTTTTTTTTTTTTTTTTTTTTAGTGTGATTCCAC    SEQ ID NO: 16
   CTTCTCA-3'

5'-NH2-(Carbon12)-TTTTTTTTTTTTTTTTTTTTTTTTTTTTTTGATTCCAC    SEQ ID NO: 17
   CTTCTCA-3'

5'-NH2-(Carbon12)-TTTTTTTTTTTTTTTTTTTTTTTTTTTTTTTTTTTCAC    SEQ ID NO: 18
   CTTCTCA-3'

Wild-type M1101K: A at 3' end
5'-NH2-(Carbon12)-TTTTTTTTTTTTTTTTAGAAGATGACAAAAATCATTT     SEQ ID NO: 19
   CTATTCTCA-3'

5'-NH2-(Carbon12)-TTTTTTTTTTTTTTTTTTTTTTTTTTAAAAATCATTT     SEQ ID NO: 20
   CTATTCTCA-3'

5'-NH2-(Carbon12)-TTTTTTTTTTTTTTTTTTTTTTTTTTTTTTTTCATTT     SEQ ID NO: 21
   CTATTCTCA-3'

5'-NH2-(Carbon12)-TTTTTTTTTTTTTTTTTTTTTTTTTTTTTTTTTCTATT    SEQ ID NO: 22
   CTCA-3'

Mutant M1101K: T at 3'end
```

```
                                              -continued
5'-NH2-(Carbon12)-TTTTTTTTTTTTTTTAGAAGATGACAAAAATCATTT     SEQ ID NO: 23

CTATTCTCT-3'

5'-NH2-(Carbon12)-TTTTTTTTTTTTTTTTTTTTTTTAAAAATCATTT      SEQ ID NO: 24

CTATTCTCT-3'

5'-NH2-(Carbon12)-TTTTTTTTTTTTTTTTTTTTTTTTTTTTCATTTCT     SEQ ID NO: 25

ATTCTCT-3'

5'-NH2-(Carbon12)-TTTTTTTTTTTTTTTTTTTTTTTTTTTTTTTTCT      SEQ ID NO: 26

ATTCTCT-3'
```

The P1 primers used for the extension may optionally have an additional mismatch at the −3 position as a means of increasing discrimination. Primer extension is readily followed using a bipolar primer (the P2 in FIG. 1) and RCA. RCA products are detected by fluorescence using a microarray slide scanner. In this example, the bipolar P2 primers have the sequence:

```
                                              SEQ ID NO: 27
G542X locus

5'-GGACATCTCCAAGTTTGCAGAGAAAGACAATATAGTTCTTTTTT

ATGATCACAGCTGAGGATAGGACATGCGA-3'
                                              SEQ ID NO: 28
M1101K locus

5'-AACTGGTTCTTGTACCTGTCAACACTGCGCTGGTTCCAAA

TTTTTCTTGTACATGTCTCAGTAGCTCGTCAGT-3'
```

The rolling circle amplification templates in this example have the sequence:

```
G542X locus: RCA will be primed by SEQ ID NO: 27

Circle 1

CGCATGTCCTATCCTCAGCTGTGATCATCAGAACTCACCTGTTAGACGCCAC   SEQ ID NO: 29

CAGCTCCAACTGTGAAGATCGCTTAT

M1101K locus: RCA will be primed by SEQ ID NO: 28

Circle 4.2

ACTGACGAGCTACTGAGACATGTACAATCGGACCTGTGAGGTACTACCCTA    SEQ ID NO: 30

ATCGGACCTGTGAGGTAOTACCCTAACTT
```

Fluorescence decorators have the following sequence:

```
                                              SEQ ID NO: 31
G542X locus:
5'-Cy3-TCAGAACTCACCTGTTAG-Cy3-C6-NH2-3'
                                              SEQ ID NO: 32
5'-Cy3-ACTGTGAAGATCGCTTAT-Cy3-C6-NH2-3'
                                              SEQ ID NO: 33
M1101k locus:
5'-Cy3-TCGGACCTGTGAGGTACTACCCTAA-Cy3-C6-NH2-3'
```

Successful allelic discrimination was defined on the basis of the ability of the primer extension/RCA process to give at least a 10-fold discrimination of mutant versus wild-type alleles.

Glass slides containing immobilized microarrays of duplicate serial dilutions of ASO P1 primers were incubated with 6.25 nM target in 10 ul of 6×SSC buffer (1×SSC buffer is 0.15 M Sodium Chloride and 0.015 M Sodium Citrate), 1% glycerol, and 100 ug/ml single-stranded salmon sperm DNA for 1 h at 45° C. The slides were then washed once for 5 min at room temperature in 100 mM NaCl, 40 mM Tris-HCl pH7.5, and 0.5 mM $MgCl_2$. The ASO P1 primers were then extended by incubation with 0.09 Units of T7 Sequenase, 100 ug/ml bovine serum albumin, 20 uM dNTPs, 100 mM NaCl, 40 mM Tris-HCl pH7.5, 1 mM DTT, and 0.5 mM $MgCl_2$ for 15 min at 37° C. The target was then removed by washing the slides twice in 0.1×SSC at 94° C. followed be a wash in 50 mM NaCl, 40 mM Tris-HCl pH7.5, 10 mM $MgCl_2$ for 5 min at room temperature.

The RCA circle (1 uM) was pre-annealed to the P2 primer (0.5 uM) in 2 ×SSC for 1 hr at 42° C. Then, the circle/primer mixture was diluted 5-fold and added to the microarrays. Annealing to the extended ASO P1 primer was at 42° C for 1 hr in RCA buffer (50 mM NaCl, 40 mM Tris-HCL pH 7.5, 10 mM $MgCl_2$). The slides were washed once at room temperature in RCA buffer for 5 min. Rolling circle amplification was then initiated by adding 6.5 Units T7 Sequenase in 10 ul RCA buffer plus 1 mM DTT, 1 mM dNTPs, 0.2 mg/mL BSA, and 5 uM SSB. The slides were incubated at 37° C. for 1 hr. RCA was terminated by washing the slide in 2×SSC for 5 min at 37° C. RCA products were detected by incubating the microarrays with 2×SSC, 0.05 uM Cy3-labelled oligonucleotide decorators (SEQ ID NO:31-33), 0.1% Tween-20, and 100 µg/mL salmon sperm DNA for 30 min at 37° C. The slides were then washed once with 2×SSC for 5 min at 37° C. and once with 0.5×SSC at room temperature for 10 seconds. The slides were dried by spinning at 1,000 rpm for 5 min on a table top clinical centrifuge. Fluorescence was measured using a microarray scanner (ScanArray 5000, GSI Lumonics, Billerica, Mass.) and spot intensity quantitated using QuantArray software (GSI Lumonics, Billerica, Mass.).

The products of RCA are readily detected by means well known in the art. Herein, they are advantageously measured fluorometrically, using a Cy3-labeled oligonucleotide that hybridizes to sequences within the template circles. Alternatively, the RCA products can be labeled using tags well known in the art, such as any one of many dNTP tags, for example, bromodexyuridine-dUTP (dBrUTP) for which the products are detected using anti-BrUdR immunoglobulin (or anti-BrUdR Ig) or biotin-dUTP for which the products are detected using an avidin-alkaline phosphatase conjugate.

In accordance with the invention disclosed herein, the target DNA is isolated as genomic DNA from a cellular source (e.g., human cell lines, blood, tissue sample, or other source of DNA, including from cells of non-humans). For purposes of the present example, this source would be human cells of known genotype for the G542 and M 1101 K loci.

The oligonucleotide primers designed as described above are then annealed to the DNA fibers followed by primer extension. The slides are then washed extensively with a suitable buffer to remove unreacted oligonucleotides. RCA is initiated by addition of the preformed circles (ATCs) of the structure already described, followed by annealing and subsequent addition of the desired DNA polymerase. Amplified DNA is then detected with one of the oligonucleotide circle-specific tags (as just described) that hybridize to the RCA product.

What is claimed is:

1. A process for detecting a single nucleotide polymorphism (SNP) in a target polynucleotide, comprising:

(a) contacting one or more allele specific oligonucleotide primers (P1) with one or more target polynucleotides (TP), wherein said target polynucleotide possesses a first portion that is complementary to a second portion located on said P1 at or near one end thereof but wherein nucleotide at said end, and third nucleotide from said end may not be complementary to the corresponding nucleotide of said target polynucleotide, and wherein such contacting occurs under conditions that promote hybridization between the first and second portions thereby forming a P1-TP complex and wherein P1 comprises the nucleotide sequence of SEQ ID NO: 13;

(b) contacting the P1-TP complex of (a) with an exonuclease deficient deoxyribonucleotide (DNA) polymerase enzyme under conditions that promote extension of the P1 with the TP as template thereby forming an extended segment (ES) of P1 only when the terminal nucleotide at the end of P1 is complementary to the corresponding nucleotide of TP; and (c) detecting the extended P1 thereby detecting an SNP in said target polynucleotide.

2. A method for determining the presence of a single nucleotide polymorphism (SNP) in a target polynucleotide comprising:

(a) contacting an allele specific oligonucleotide primer (P1) with a target polynucleotide (TP), under conditions supporting hybridization between P1 and TP, wherein said TP possesses a portion complementary to a segment of P1 at or near one end of P1 but wherein the nucleotide at said end, and third nucleotide from said end may independently be non-complementary to the corresponding nucleotide of TP and forming a P1-TP hybridized complex;

(b) contacting the P1-TP complex of (a) with an exonuclease deficient deoxyribonucleotide (DNA) polymerase enzyme under conditions supporting extension of P1 with TP as template to form an extended segment (ES) of P1 only when the terminal nucleotide at the end of P1 is complementary to the corresponding nucleotide of TP;

(c) determining the extended P1 by removing the target polynucleotide from the complex formed in step (b) and contacting a primer oligonucleotide (P2) with the extended P1, wherein P2 comprises a portion that hybridizes to the extended segment of P1 and a portion that does not and then contacting an amplification target circle (ATC) with said P1-P2 wherein the ATC hybridizes to the portion of P2 that does not hybridize to extended P1 and under conditions promoting rolling circle amplification of the ATC with P2 as primer thereby extending P2 to form TS-DNA wherein said method does not include a ligation reaction and whereby TS-DNA formation indicates extension of P1 in step (b) and thus the presence or absence of a polymorphism in TG.

3. The method of claim 2 wherein P2 comprises two 3'-ends.

4. The method of claim 2 wherein the target polynucleotide is derived from genomic DNA.

5. The method of claim 4 wherein the genomic DNA comprises human genomic DNA.

6. The method of claim 4 wherein the genomic DNA comprises non-human genomic DNA.

7. The method of claim 2 wherein the exonuclease-deficient DNA polymerase is T7 Sequenase or Tth polymerase.

8. The method of claim 2 wherein P1 is attached to a solid support.

9. The process of claim 8 wherein the solid support is composed of at least one member selected from the group consisting of acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids.

10. The method of claim 8 wherein the solid support is made of glass or plastic.

11. The process of claim 2 wherein P1 is selected from the group consisting of the sequences of SEQ ID NOs: 1, 2, 3, 4, 11, 12, 13, 14, 15, 16, 17, 18, 19, 20, 21, 22, 23, 24, 25, and 26.

12. A method for diagnosing a disease characterized by a mutated gene sequence comprising:
   (a) obtaining a sample of a mutated gene sequence from an animal afflicted with said disease; and
   (b) applying the method of claim 2 wherein at least a portion of said mutated gene sequence is used as either the target polynucleotide (TP) or the allele specific oligonucleotide (P1).

13. The method of claim 12 wherein the mutated gene sequence is used as the target polynucleotide.

14. The method of claim 12 wherein said animal is a human.

15. The method of claim 12 wherein said disease is a disease caused by, induced by or related to a mutation in at least one gene.

16. The method of claim 15 wherein said disease is a member selected from the group consisting of Parkinson's disease, Duchenne muscular dystrophy, Niemann-Pick disease, polyposis, neurofibromatosis, polycystic kidney disease, Tay-Sachs disease, xeroderma pigmentosa, ataxia-telangiectasia, Huntington disease, Li-Fraumeni syndrome, beta-thalassemia, sickle cell anemia, hemoglobin C disease, hemophilia, acute intermittent porphyria, cystic fibrosis, diabetes, obesity and cancer.

17. The method of claim 16 wherein said cancer is a member selected from the group consisting of leukemia, lymphoma, melanoma, neuroblastoma, retinoblastoma, rhabdomyosarcoma, Ewing sarcoma, head and neck cancer, skin cancer, brain cancer, esophageal cancer, stomach cancer, lung cancer, breast cancer, colon cancer, ovarian cancer, testicular cancer and prostate cancer.

18. The method of claim 2 wherein the third nucleotide from the end of said P1 is complementary to the corresponding nucleotide of the target polynucleotide.

19. The method of claim 2 wherein the third nucleotide from the end of said P1 is not complementary to the corresponding nucleotide of TP.

20. The method of claim 2 wherein both the terminal nucleotide and third nucleotide from the end of P1 are not complementary to the corresponding nucleotide of TP.

* * * * *

SEQUENCE LISTING

<160> NUMBER OF SEQ ID NOS: 35

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 1
ctcagtgtga ttccaccttc tcc                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 2
ctcagtgtga ttccaccttc acc                                            23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 3
ctcagtgtga ttccaccttc tca                                            23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 4
ctcagtgtga ttccaccttc aca                                            23

<210> SEQ ID NO 5
<211> LENGTH: 96

```
<212> TYPE: DNA
<213> ORGANISM: Artificial Sequence
<220> FEATURE:
<223> OTHER INFORMATION: Description of Artificial Sequence: Target
      polynucleotide for allele discrimination

<400> SEQUENCE: 5
gacgagtcag aatcagagaa agacaatata gttcttggag aaggtggaat cacactgagc      60
cctatagtga gtcgtattaa actaaagctg agacat                                96

<210> SEQ ID NO 6
<211> LENGTH: 96
<212> TYPE: DNA
<213> ORGANISM: Artificial Sequence
<220> FEATURE:
<223> OTHER INFORMATION: Description of Artificial Sequence: Target
      polynucleotide for allele discrimination

<400> SEQUENCE: 6
gacgagtcag aatcagagaa agacaatata gttctttgag aaggtggaat cacactgagc      60
cctatagtga gtcgtattaa actaaagctg agacat                                96

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Target
      polynucleotide for allele discrimination

<400> SEQUENCE: 7
taataggaca tctccaagtt tgcagagaaa gacaatatag ttcttggaga aggtggaatc      60
acactgagtg gaggtcaacg                                                  80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Target
      polynucleotide for allele discrimination

<400> SEQUENCE: 8
taataggaca tctccaagtt tgcagagaaa gacaatagag ttctttgaga aggtggaatc      60
acactgagtg gaggtcaacg                                                  80

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence: Target
      polynucleotide for allele discrimination

<400> SEQUENCE: 9
caactggttc ttgtacctgt caacactgcg ctggttccaa atgagaatag aaatgatttt      60
tgtcatct                                                               68

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: Target
``` polynucleotide for allele discrimination

<400> SEQUENCE: 10
caactggttc ttgtacctgt caacactgcg ctggttccaa agagaatag aaatgatttt      60 tgtcatct                                                              68

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 11
tttttttttt ttttaccctc cactcagtgt gattccacct tctcc                     45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 12
tttttttttt tttttttttt tttttagtgt gattccacct tctcc                     45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 13
tttttttttt tttttttttt tttttttttt gattccacct tctcc                     45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 14
tttttttttt tttttttttt tttttttttt tttttcacct tctcc                     45

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 15
tttttttttt ttttaccctc cactcagtgt gattccacct tctca                     45

<210> SEQ ID NO 16
<211> LENGTH: 45
<212> TYPE: DNA
<213> ORGANISM: Artificial Sequence
<220> FEATURE:

<223> OTHER INFORMATION: Description of Artificial Sequence: P1 primer
      for use in allele discrimination

<400> SEQUENCE: 16
tttttttttt tttttttttt tttttagtgt gattccacct tctca                45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 17
tttttttttt tttttttttt tttttttttt gattccacct tctca                45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 18
tttttttttt tttttttttt tttttttttt tttttcacct tctca                45

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 19
tttttttttt tttttagaa gatgacaaaa atcatttcta ttctca                46

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 20
tttttttttt tttttttttt tttttttaaaa atcatttcta ttctca               46

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 21
tttttttttt tttttttttt tttttttttt ttcatttcta ttctca                46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: P1 primer

```
         for use in allele discrimination

<400> SEQUENCE: 22
tttttttttt tttttttttt tttttttttt tttttttcta ttctca            46

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 23
tttttttttt tttttagaa gatgacaaaa atcatttcta ttctct             46

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 24
tttttttttt tttttttttt tttttaaaa atcatttcta ttctct             46

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 25
tttttttttt tttttttttt tttttttttt ttcatttcta ttctct            46

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: P1 primer
      for use in allele discrimination

<400> SEQUENCE: 26
tttttttttt tttttttttt tttttttttt tttttttcta ttctct            46

<210> SEQ ID NO 27
<211> LENGTH: 73
<212> TYPE: DNA
<213> ORGANISM: Artificial Sequence
<220> FEATURE:
<223> OTHER INFORMATION: Description of Artificial Sequence: Primer for
      use in rolling circle amplification

<400> SEQUENCE: 27
ggacatctcc aagtttgcag agaaagacaa tatagttctt ttttatgatc acagctgagg    60
ataggacatg cga                                                      73

<210> SEQ ID NO 28
<211> LENGTH: 73
<212> TYPE: DNA
<213> ORGANISM: Artificial Sequence
<220> FEATURE:
```

-continued

<223> OTHER INFORMATION: Description of Artificial Sequence: Primer for
use in rolling circle amplification

<400> SEQUENCE: 28
aactggttct tgtacctgtc aacactgcgc tggttccaaa tttttcttgt acatgtctca    60
gtagctcgtc agt                                                      73

<210> SEQ ID NO 29
<211> LENGTH: 78
<212> TYPE: DNA
<213> ORGANISM: Artificial Sequence
<220> FEATURE:
<223> OTHER INFORMATION: Description of Artificial Sequence:
Amplification target circle sequence for use in rolling circle
amplification

<400> SEQUENCE: 29
cgcatgtcct atcctcagct gtgatcatca gaactcacct gttagacgcc accagctcca    60
actgtgaaga tcgcttat                                                  78

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence:
Amplification target circle sequence for use in rolling circle
amplification

<400> SEQUENCE: 30
actgacgagc tactgagaca tgtacaatcg gacctgtgag gtactaccct aatcggacct    60
gtgaggtact accctaactt                                                80

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Nucleotide
sequence for use as fluorescence decorator.

<400> SEQUENCE: 31
tcagaactca cctgttag                                                  18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Nucleotide
sequence for use as fluorescence decorator.

<400> SEQUENCE: 32
actgtgaaga tcgcttat                                                  18

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Nucleotide
sequence for use as fluorescence decorator.

<400> SEQUENCE: 33
tcggacctgt gaggtactac cctaa                                          25

<210> SEQ ID NO 34
<211> LENGTH: 57
<212> TYPE: DNA
<213> ORGANISM: Artificial Sequence
<220> FEATURE:
<223> OTHER INFORMATION: Description of Artificial Sequence: Primer for
      use in rolling circle amplification

<400> SEQUENCE: 34
gttcttgata taacagaaag ttttttttat gatcacagct gaggatagga catgcga          57

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Primer for
      use in rolling circle amplification

<400> SEQUENCE: 35
tttcttgata taacagaaag ttttttttct tgtacatgtc tcagtagctc gtcagt           56